United States Patent
Gonzalez

(10) Patent No.: US 10,646,116 B2
(45) Date of Patent: May 12, 2020

(54) IN SITU DETERMINATION OF REFRACTIVE INDEX OF MATERIALS

(71) Applicant: OptiMedica Corporation, Santa Ana, CA (US)

(72) Inventor: Javier Gonzalez, Palo Alto, CA (US)

(73) Assignee: AMO Development, LLC, Santa Ana, CA (US)

( * ) Notice: Subject to any disclaimer, the term of this patent is extended or adjusted under 35 U.S.C. 154(b) by 1259 days.

(21) Appl. No.: 14/327,839

(22) Filed: Jul. 10, 2014

(65) Prior Publication Data

US 2015/0032090 A1     Jan. 29, 2015

Related U.S. Application Data

(60) Provisional application No. 61/858,445, filed on Jul. 25, 2013.

(51) Int. Cl.
*A61B 3/103* (2006.01)
*A61B 3/10* (2006.01)
(Continued)

(52) U.S. Cl.
CPC ............... *A61B 3/103* (2013.01); *A61B 3/10* (2013.01); *A61F 9/00825* (2013.01);
(Continued)

(58) Field of Classification Search
CPC ......... A61B 3/10; A61B 3/1005; A61B 3/102; A61B 3/103; A61F 9/008; A61F 9/00804;
(Continued)

(56) References Cited

U.S. PATENT DOCUMENTS

| 5,459,570 A | 10/1995 | Swanson et al. |
| 5,720,894 A | 2/1998 | Neev et al. |

(Continued)

FOREIGN PATENT DOCUMENTS

| DE | 202012002375 U1 | 4/2012 |
| GB | 2409033 A | 6/2005 |

(Continued)

OTHER PUBLICATIONS

International Search Report and Written Opinion for Application No. PCT/US2014/046113, dated Oct. 10, 2014, 13 pages.
(Continued)

*Primary Examiner* — Ahmed M Farah
(74) *Attorney, Agent, or Firm* — Johnson & Johnson Surgical Vision, Inc.

(57) ABSTRACT

A laser eye surgery system focuses light along a beam path to a focal point having a location within a lens of the eye. The refractive index of the lens is determined in response to the location. The lens comprises a surface adjacent a second material having a second refractive index. The beam path extends a distance from the surface to the focal point. The index is determined in response to the distances from the surface to the targeted focal point and from the surface to the actual focal point, which corresponds to a location of a peak intensity of an optical interference signal of the focused light within the lens. The determined refractive index is mapped to a region in the lens, and may be used to generate a gradient index profile of the lens to more accurately place laser beam pulses for incisions.

20 Claims, 11 Drawing Sheets

(51) Int. Cl.
*A61F 9/008* (2006.01)
*G01M 11/02* (2006.01)
*G01N 21/45* (2006.01)

(52) U.S. Cl.
CPC .............. *A61B 3/102* (2013.01); *A61B 3/1005* (2013.01); *G01M 11/0228* (2013.01); *G01N 21/45* (2013.01)

(58) Field of Classification Search
CPC ........ A61F 9/00825; A61F 2009/00861; A61F 2009/00863; A61F 2009/0087; A61F 2009/00872; A61F 2009/00874; A61F 2009/00876; G01N 21/41; G01N 2021/41; G01N 21/4133; G01N 21/45; G01M 11/005; G01M 11/02; G01M 11/0221; G01M 11/0228
USPC ....... 606/4–6, 10–12; 351/205–212; 128/898
See application file for complete search history.

(56) References Cited

U.S. PATENT DOCUMENTS

| | | | |
|---|---|---|---|
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A | 4/2000 | Wei et al. | |
| 6,111,645 A | 8/2000 | Tearney et al. | |
| 6,454,761 B1 | 9/2002 | Freedman | |
| 6,508,960 B1* | 1/2003 | Ohmer ................... C30B 29/46 | 252/582 |
| 7,217,375 B2* | 5/2007 | Lai ......................... A61B 3/028 | 264/1.1 |
| 7,655,002 B2 | 2/2010 | Myers et al. | |
| 7,717,907 B2 | 5/2010 | Ruiz et al. | |
| 8,218,152 B1 | 7/2012 | Marks et al. | |
| 8,262,646 B2 | 9/2012 | Frey et al. | |
| 8,350,183 B2 | 1/2013 | Vogel et al. | |
| 8,377,047 B2* | 2/2013 | Dai ........................ A61F 9/008 | 128/898 |
| 8,382,745 B2 | 2/2013 | Naranjo-Tackman et al. | |
| 8,414,564 B2 | 4/2013 | Goldshleger et al. | |
| 8,500,724 B2 | 8/2013 | Blumenkranz et al. | |
| 9,721,351 B2 | 8/2017 | Gonzalez et al. | |
| 9,996,938 B2 | 6/2018 | Gonzalez et al. | |
| 10,085,886 B2 | 10/2018 | Schuele et al. | |
| 10,190,977 B2* | 1/2019 | Marcus ................... G01N 21/45 | |
| 10,485,704 B2* | 11/2019 | Scott ....................... A61B 3/107 | |
| 2005/0203422 A1 | 9/2005 | Wei | |
| 2006/0206102 A1 | 9/2006 | Shimmick | |
| 2008/0033408 A1* | 2/2008 | Bueler ..................... A61F 9/008 | 606/5 |
| 2008/0039825 A1* | 2/2008 | Lai .......................... A61B 3/107 | 606/5 |
| 2008/0281303 A1 | 11/2008 | Culbertson et al. | |
| 2009/0242021 A1* | 10/2009 | Petkie ............... H01L 31/02168 | 136/256 |
| 2010/0171865 A1* | 7/2010 | Toda .................. B29D 11/00009 | 348/340 |
| 2011/0319873 A1 | 12/2011 | Raksi et al. | |
| 2011/0319875 A1 | 12/2011 | Loesel et al. | |
| 2012/0069298 A1* | 3/2012 | Ng ......................... A61B 3/0025 | 351/206 |
| 2012/0120408 A1 | 5/2012 | Yasuno et al. | |
| 2012/0268714 A1* | 10/2012 | Cameron ........... A61B 5/14558 | 351/206 |
| 2013/0165911 A1 | 6/2013 | Raksi et al. | |
| 2014/0343541 A1 | 11/2014 | Scott et al. | |
| 2015/0018674 A1 | 1/2015 | Scott et al. | |
| 2015/0141972 A1* | 5/2015 | Woodley ................ A61B 3/102 | 606/5 |

FOREIGN PATENT DOCUMENTS

| | | |
|---|---|---|
| JP | 2003052632 A | 2/2003 |
| JP | 2011502585 A | 1/2011 |
| JP | 2012521237 A | 9/2012 |
| JP | 2013517844 A | 5/2013 |
| JP | 2013520236 A | 6/2013 |
| WO | 2015013044 A1 | 1/2015 |
| WO | 2016061454 A1 | 4/2016 |

OTHER PUBLICATIONS

International Search Report and Written Opinion for Application No. PCT/US2016/052543, dated Jun. 13, 2017, 13 pages.

* cited by examiner

IN SITU DETERMINATION OF REFRACTIVE INDEX OF MATERIALS

CROSS-REFERENCE

This application claims the benefit of priority to U.S. Provisional Patent Application No. 61/858,445, filed on Jul. 25, 2013, which is related to the following patent applications: U.S. patent application Ser. No. 12/048,182, filed Mar. 3, 2008, entitled "METHOD AND APPARATUS FOR CREATING INCISIONS TO IMPROVE INTRAOCULAR LENS PLACEMENT," U.S. patent application Ser. No. 12/048,186, filed Mar. 13, 200, entitled "METHOD AND APPARATUS FOR CREATING OCULAR SURGICAL AND RELAXING INCISIONS," and U.S. Patent Application Ser. No. 61/722,064, filed Nov. 2, 2012, entitled "LASER EYE SURGERY SYSTEM CALIBRATION," the entirety of which are hereby incorporated by reference.

BACKGROUND

The present disclosure relates generally to photodisruption induced by a pulsed laser beam and the location of the photodisruption so as to treat a material, such as a tissue of an eye. Although specific reference is made to locating target site(s) for photodisruption and cutting tissue for surgery such as eye surgery, embodiments as described herein can be used in many ways with many materials to treat one or more of many materials, such as cutting of optically transparent materials.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Pulsed lasers can be used to cut one or more of many materials and have been used for laser surgery to cut tissue.

Examples of surgical tissue cutting include cutting the cornea and crystalline lens of the eye. The lens of the eye can be cut to correct a defect of the lens, for example to remove a cataract, and the tissues of the eye can be cut to access the lens. For example the cornea can be cut to access the cataractous lens. The cornea can be cut in order to correct a refractive error of the eye, for example with laser assisted in situ keratomileusis (hereinafter "LASIK").

Many patients may have less than ideal optics of the eye. At least some patients may have refractive error of the eye that can be corrected with spectacles and contact lenses, for example. However, patients may have an irregularity of the cornea of eye such as irregular astigmatism or corneal scarring from example. In at least some instances, the irregularity of the eye may not be easily corrected with prior methods and apparatus. Prior approaches to treating the diseased cornea have included keratoplasty, such as penetrating keratoplasty (hereinafter "PK"), for example. The prior keratoplasty procedures can result in less than ideal patient outcomes in at least some instances. For example, patients may have less than ideal visual acuity after keratoplasty procedures. In at least some instances, such less than ideal visual acuity may be caused than less than ideal positioning and location of tissue cuts.

Prior short pulse laser systems have been used to cut tissue, and have been used to treat many patients. However, the prior short pulse systems may provide less than ideal results in at least some instances. For example, the alignment of the eye with the laser surgery system can be less than ideal in at least some instances, such as when refractive treatment of the cornea of the eye is combined with a treatment of the lens of the eye such as removal of the cortex and nucleus from the eye. In another example, the laser eye surgery system may not properly take into account the different indices of refraction of the eye anatomy in at least some instances, which may affect the positioning of tissue cuts in at least some instances.

In order to more accurately treat the eye, prior methods and apparatus have combined optical measurement systems such as tomography systems. However, the accuracy of such prior measurement devices can be less than ideal in at least some instances. For example, to determine the physical location of a structure, the prior devices may rely on an assumed index of refraction which can vary from the actual index of refraction of the particular eye of an individual being treated. Further, at least some prior devices may rely on an assumed average value of the index of refraction for tissues that have a varying index of refraction such as tissue of the lens. The amount of variation of the index of refraction within an individual may vary more, or less, than normative values for a population, potentially making assumed values less accurate in at least some instances. In at least some instances, the treatment beam may comprise different wavelengths than the measurement beam, potentially further compounding the errors in the measurements in at least some instances.

The decreased accuracy of the prior methods an apparatus may limit, in at least some respects, the treatment of the prior methods and apparatus. For example, variability of the index of refraction may result in variability of the depth at which tissue is incised, thereby potentially decreasing the accuracy of the prior surgical procedures and potentially limiting the use of lasers to incise tissue near sensitive.

In light of the above, it would be desirable to provide improved methods and apparatus that overcome at least some of the above limitations of the above prior systems and methods. Ideally, these improved systems and methods will provide in situ measurement of the index of refraction of optically transmissive materials, provide improved measurement of the location of structures within the optically transmissive materials, and provide improved treatment with more accurate focus of laser beams within the material.

SUMMARY

The disclosure provides systems, devices, and methods for determining an index of refraction of a material such as one or more anatomical structures of an eye of a subject, for example, the lens of the eye. In many embodiments, the index of refraction of one or more tissue structures is measured in order to more accurately treat the tissue. The index of refraction can be determined in order to more accurately treat the material, and the index of refraction may be determined along an optical beam path of a treatment beam in order to more accurately treat the material. The index of refraction along the beam path may comprise an average index of refraction, or a plurality of indices of refraction mapped to locations of the material. In many embodiments, the refractive index is determined in situ with a first light beam having one or more first wavelengths, and a second light beam such as a laser beam having second one or more wavelengths of light different from the first one or more wavelengths is used to treat the tissue. One or more components of an optical system may focus light along a beam path to a focal point having a location within the material. The index of refraction of the material may be determined in response to the location of the focal point within the material. Although the focal point can be determined in one or more of many ways, in many embodiments, the focal point is determined with an intensity of an interference signal related to coherence of the light beam, such that the focal point and corresponding index of refraction can be accurately measured. The material may comprise a surface adjacent a second material having a second index of refraction, and the beam path may extend a distance from the surface to the focal point. The index may be determined in response to the distances from the surface to the targeted focal point and from the surface to the actual focal point, which may correspond to a location of a peak intensity of an optical coherence signal of the focused light within the material. The determined index of refraction may be mapped to a region in the material. A plurality of determined indices can be used to generate an index profile of the material, such as a gradient index profile of the material. This gradient index profile can be utilized by the laser system to position laser beam focal points within the material to more accurately place incisions.

Embodiments described herein may be well suited for cataract surgery in response to the measured index or indices of refraction, retinal surgery in response to the measured index or indices of refraction, vitreo-retinal surgery in response to the measured index or indices of refraction, glaucoma surgery in response to the measured index or indices of refraction, refractive eye surgery in response to the measured index or indices of refraction, corneal surgery in response to the measured index or indices of refraction, and many other eye surgery procedures in response to the measured index or indices of refraction.

An aspect of the disclosure provides a method of determining an index of refraction of a material. Light can be focused along a beam path to a focal point having a location within the material, and the index of refraction of the material is determined in response to the location of the focal point within the material. The material may comprise a surface adjacent a second material having a second index of refraction, with the first index of refraction being different from the second index of refraction. The beam path may extend a distance from the surface to the focal point. The index may be determined in response to the distance from the surface to the focal point. The material may comprise a target material. And, the location of the beam path may be determined with an optical interference signal of the focused light, for example, in response to a location of a peak intensity of the optical interference signal.

In many embodiments, the target material comprises an optically transmissive tissue structure of an eye of a subject. The optically transmissive tissue structure of the eye may comprise one or more of a tear film, a cornea, an aqueous humor, a lens, an anterior lens capsule, a lens cortex, an anterior portion of the lens cortex, a posterior portion of the lens cortex, a lens nucleus, a posterior lens capsule, or a vitreous humor. A second tissue structure may comprise the second material, the second tissue structure anterior to the optically transmissive tissue structure with the surface disposed in between. A plurality of locations of a plurality of focal points along the beam path may be determined in order to determine the index of refraction of the optically transmissive tissue structure. The plurality of locations may comprise a first location of a first focal point and a second location of a second focal point. The index of refraction may correspond to an average index of refraction of the material between the first point and the second point.

In some embodiments, the first location comprises an anterior location of an anterior portion of a lens of the eye and a second location comprises a posterior location of a posterior portion of the eye. The index of refraction may correspond to an average index of refraction between the anterior portion of the lens and the posterior portion of the lens. The average index may correspond to an integral of the index of refraction along an optical path length between the anterior location and the posterior location in order to determine positioning of a treatment beam near a posterior capsule of the lens. A plurality of focused laser beam pulses may be directed to a posterior portion of the lens to incise the posterior portion of the lens. A plurality of focused laser beam pulses may be directed to a posterior capsule of the lens to incise the posterior capsule of the lens in response to the average index of refraction. The focused beam may comprises one or more wavelengths of light different than the focused laser beam.

In some embodiments, the index of refraction of the tissue structure is mapped in response to the plurality of locations of the plurality of focal points along the beam path. The focusing and determining steps may be repeated for each of the plurality of focal points in order to determine the index of refraction of the target material for said each of the plurality of locations. The plurality of locations may comprise locations of the lens of the eye. A gradient index profile of the lens of the eye may be determined in response to the plurality of locations of the plurality of focal points within the lens of the eye.

In many embodiments, the light source comprises a light source of a tomography system. The tomography system may comprise one or more of an optical coherence tomography system, a spectral optical coherence tomography system, a time domain optical coherence tomography system, a Scheimpflug imaging tomography system, a confocal tomography system, or a low coherence reflectometry system. The location of the focal point may be determined with the tomography system.

In many embodiments, the index of refraction of the target material is determined in response to a predetermined index of refraction. The predetermined index of refraction may comprise the index of refraction of one or more of a patient interface optic, water, saline, cornea, or aqueous humor. The index of refraction may be calculated by multiplying the predetermined index of refraction with a square root of a distance between a surface of the target material and the determined beam path location divided by a distance between the surface of the target material and the intended focal point.

Another aspect of the disclosure provides a method of treating a structure of an eye. A light source is focused into the structure to a focal point having a location. A location of the focal point is identified in response to an optical interference signal. An index of refraction of the material is determined in response to the location of the focal point. The index of refraction is mapped to the structure. A profile of the structure is determined in response to the mapping. The structure is incised in response to the profile of the structure. The structure of the eye may comprise one or more of a tear film, a cornea, an aqueous humor, a lens, a posterior lens capsule, a posterior lens capsule, a lens cortex, a lens nucleus, or a vitreous humor.

Yet another aspect of the disclosure provides an apparatus for determining an index of refraction of a material. The apparatus comprises a tomography system and a processor. The tomography system comprises a light source to generate a beam of light. The processor comprises a tangible medium coupled to the imaging system and configured to receive data from the tomography system. The tangible medium embodies instructions to determine an index of refraction of material in response to a location of a focal point of the beam.

In many embodiments, the tangible medium further embodies instructions to: focus the light beam into the material to an intended focal point having an intended location, identify a location of an interference signal of the focused light, determine an index of refraction of the target material in response to the intended focal point location and the determined interference pattern location, and map the determined index of refraction to the location of the material.

In many embodiments, the apparatus further comprises a pulsed laser and an optical delivery system. The pulsed laser can generate a pulsed laser beam to incise the material. The optical delivery system is coupled to the laser beam, the tomography system, and the processor. The tangible medium may further comprise instructions to determine a treatment profile in response to the index of refraction. In some embodiments, the pulsed laser comprises first one or more wavelengths and the second laser comprises second one or more wavelengths different from said first one or more wavelengths. And, the processor comprises instructions to determine a plurality of focus positions of the pulsed laser beam comprising the second one or more wavelengths in response to the index of refraction of the first one or more wavelengths. In some embodiments, the tangible medium further embodies instructions to determine a profile of the material in response to the mapping and incise the material in response to the profile of the material with the laser. In some embodiments, the processor embodies instructions to determine instructions of an incision profile of a second structure posterior to the material in response to the index of refraction of the material.

In many embodiments, the tangible medium embodies instructions to determine a plurality of indices of refraction of a plurality of tissue structures of an eye along an optical path to a targeted tissue structure of an eye. The tangible medium may embody instructions to determine a focus position of a pulsed laser beam to incise tissue in response to the plurality of indices of refraction along the optical path. The plurality of tissue structures may comprise one or more of a tear film, a cornea, an aqueous humor, a lens, an anterior lens capsule, an anterior lens cortex, a lens nucleus, a posterior lens cortex, a posterior lens capsule or a vitreous humor of the eye.

In many embodiments, the tomography system comprises one or more of an optical coherence tomography system, a spectral optical coherence tomography system, a time domain optical coherence tomography system, a Scheimpflug imaging tomography system, a confocal tomography system, or a low coherence reflectometry system and wherein the location of the focal point is determined with the tomography system.

The claims provided herein provide additional aspects in accordance with embodiments and are incorporated herein by reference.

DETAILED DESCRIPTION

Figure 1:
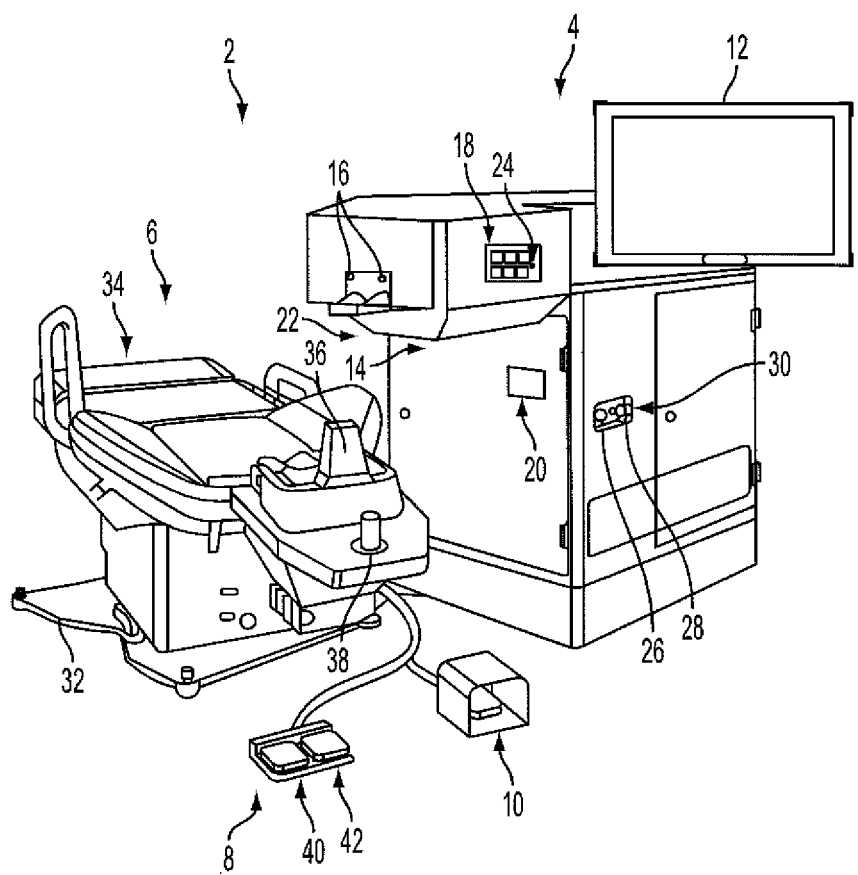
FIG. 1 shows a perspective view showing a laser eye surgery system, in accordance with many embodiments.

Methods and systems related to laser eye surgery are disclosed. In many embodiments, a laser is used to form precise incisions in the cornea, in the lens capsule, and/or in the crystalline lens nucleus. Although specific reference is made to tissue resection for laser eye surgery, embodiments as described herein can be used in one or more of many ways with many surgical procedures and devices, such as orthopedic surgery, robotic surgery and microkeratomes.

The embodiments as described herein are particularly well suited for mapping the index of refraction with a first beam having first one or more wavelengths of light. The mapped index of refraction can be used to determine the physical location of the tissue structure, in response to a mapped index of refraction along the measurement beam path extending to the tissue structure, for example.

A laser may be used to form precise incisions in the cornea, in the lens capsule, and/or in the crystalline lens nucleus, for example. The embodiments as described herein can be particularly well suited for increasing the accuracy of the cutting of the material such as tissue, for example. For example, the mapped index of refraction can be used to determine the location of one or more components of the laser system such as a lens and movable mirrors in order to more accurately place the laser beam focus and tissue incisions. In many embodiments, tissue structures are mapped with a beam of a measurement system such as a tomography system and the index of refraction of the tissue is mapped with the focused measurement beam as described herein. The tissue structures mapped with the measurement beam can be adjusted in response to the mapped indices of refraction from the focused measurement beam in order to more accurately determine the physical locations of the tissue structures.

The physical locations and dimensions of the tissue structures of the eye and the mapped indices of refraction can be used to more accurately determine the positions of the laser system components. For example, the laser beam incision profile of the tissue of the eye can be determined in response to physical locations of tissue structures or the locations of the structures from tomography images, and combinations thereof. In many embodiments, the mapped indices of refraction determined with the focused measurement beam having first one or more wavelengths are adjusted in response to an index of refraction of the laser treatment beam having second one or more wavelengths in order to provide mapping of the index of refraction for the treatment beam. The range of the first one or more wavelengths can overlap with the range of the second one or more wavelengths such that the wavelengths are similar, or have non-overlapping ranges such that the first one or more wavelengths differs from the second one or more wavelengths. The mapped index of refraction of the treatment beam can be combined with one or more of the physical locations and dimensions of the tissue structures, the targeted incision profile, or the mapped index of refraction of the focused measurement beam, in order to determine the positions of the mirrors and lenses of the laser treatment system to place the laser beam incisions at the targeted locations of the eye.

In many embodiments, the index of refraction of the treatment beam can be determined by adjusting the measured index of refraction of the measurement beam to correct for differences in the indices of refraction of the treatment beam and measurement beam. Alternatively or in combination a baseline index of refraction of the treatment beam can be adjusted in response to the index of refraction measured with the measurement beam. In many embodiments, a baseline index of refraction is adjusted in response to the measured index of refraction. The baseline index of refraction may comprise an index of refraction of a structure of the eye. While the index of refraction of tissue such as eye can vary with wavelength as described herein, approximate baseline values include: aqueous humor 1.33; cornea 1.38; vitreous humor 1.34; and lens 1.36 to 1.41, in which the index of the lens can differ for the capsule, the cortex and the nucleus, for example. The baseline phase indices of refraction of water and saline can be about 1.325 for the ultrafast laser at 1030 nm and about 1.328 for the OCT system at 830 nm, and this proportional difference can be used to determine the index of refraction of the treatment beam in response to the index of refraction measured with the measurement beam, for example. The group refractive index of 1.339 differs on the order of 1% for the OCT beam wavelength and spectral bandwidth. Many embodiments herein provide methods and apparatus for determining the indices of refraction, the phase indices of refraction, and group indices of refraction of the tissues of the eye for the wavelengths of the measurement and treatment systems as described herein.

The embodiments disclosed herein are well suited for combination with prior laser surgery systems, such as Catalys™ commercially available from Optimedica, and similar systems. Such systems can be modified in accordance with the teachings disclosed herein and to more accurately measure and treat the eye.

As used herein like characters such as reference numerals and letters described like elements.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

The processor system may comprise tangible medium embodying instructions of a computer program to perform one or more of the method steps as described herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
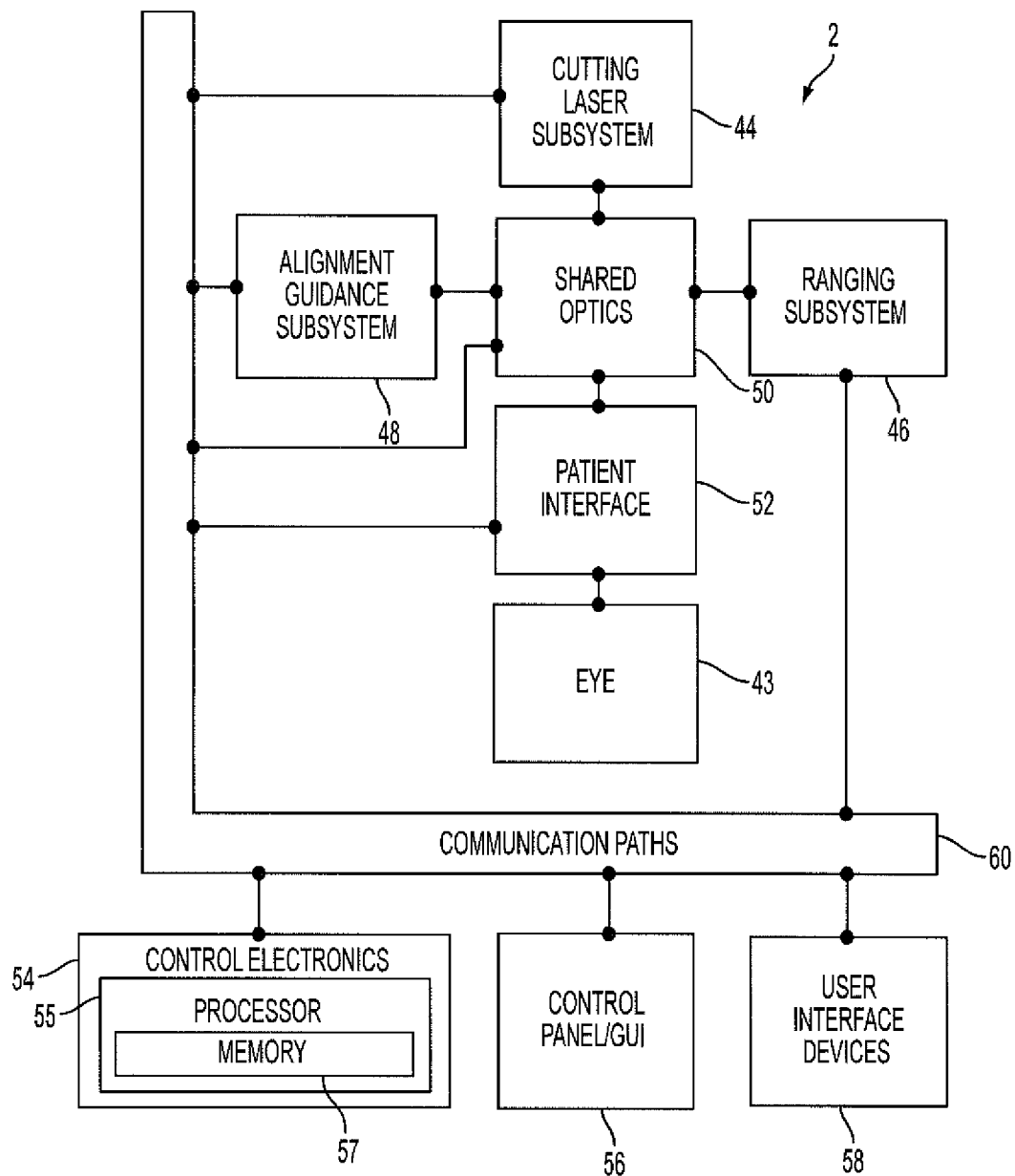
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 43I. The iris 43I defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 52 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
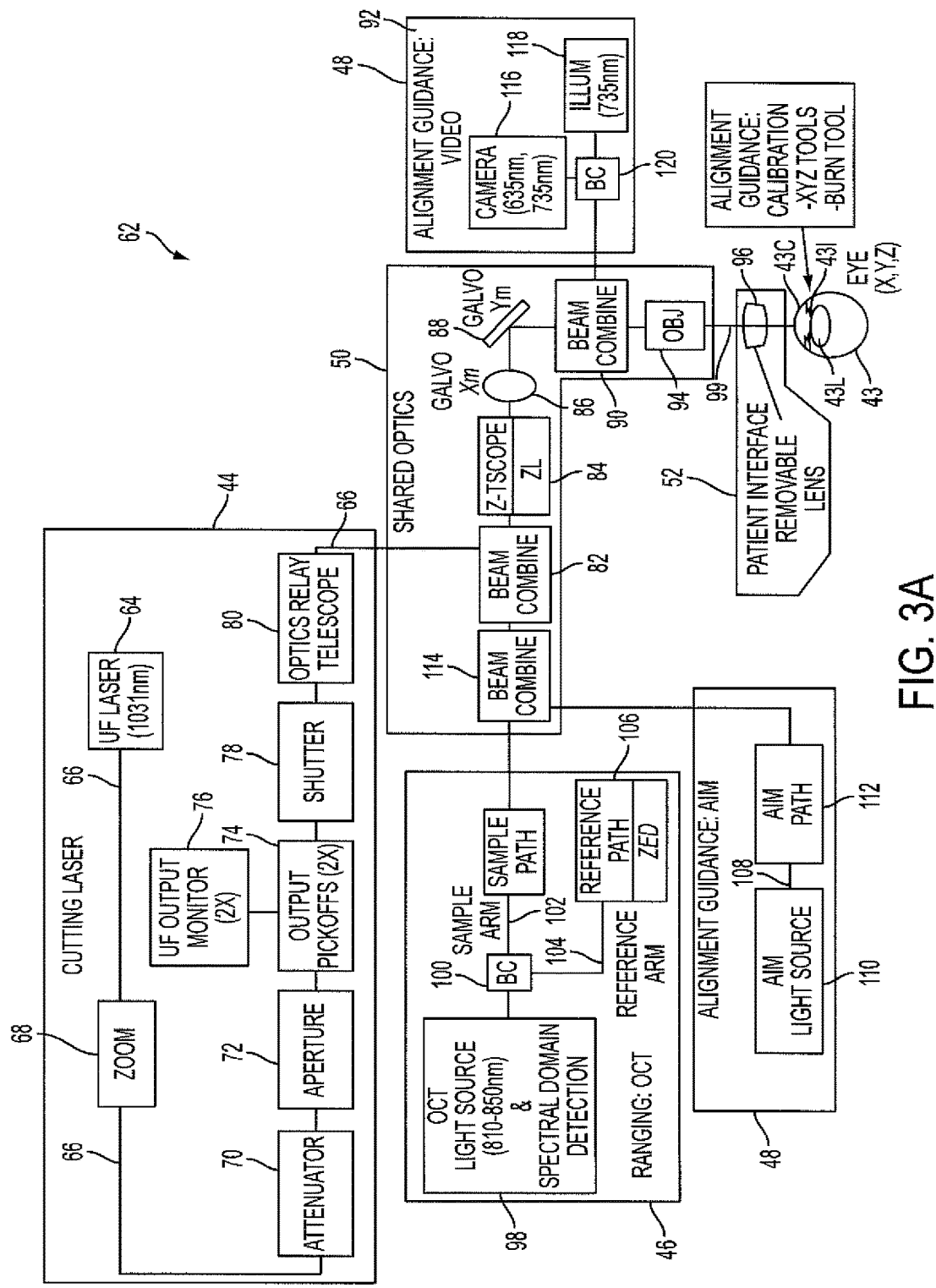
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structures of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3 includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
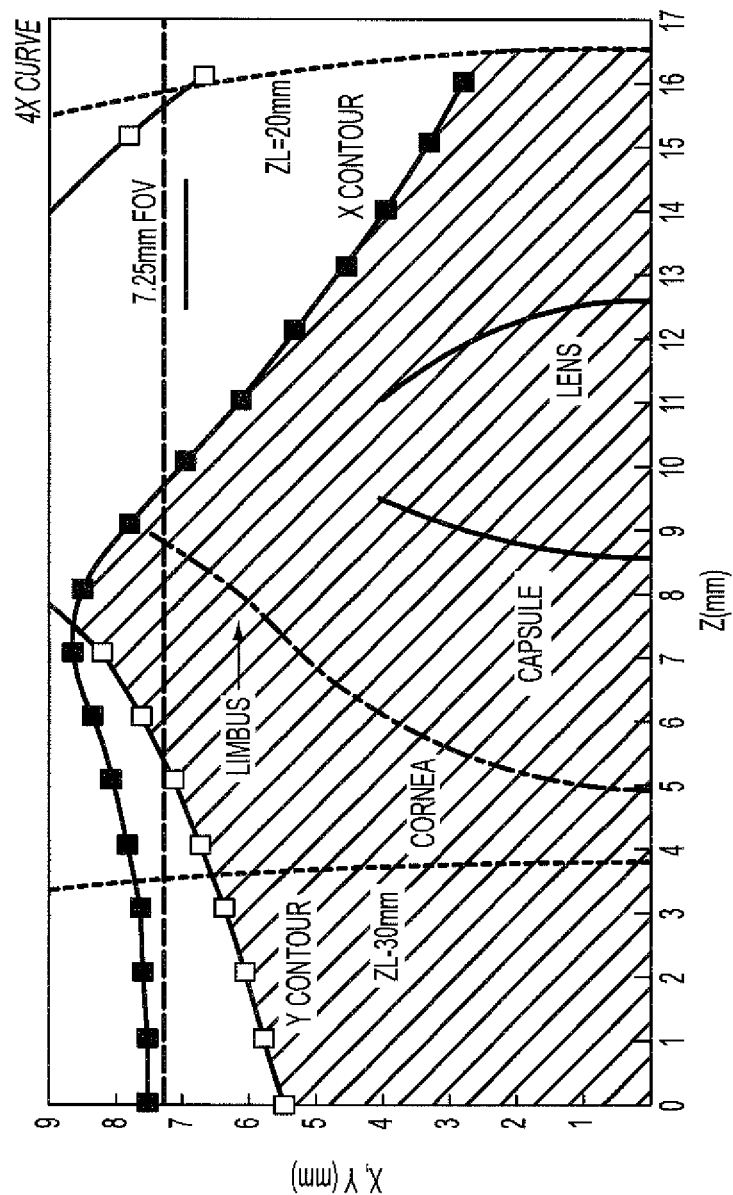
FIG. 3B shows a mapped treatment region of the eye comprising the cornea, the posterior capsule, and the limbus, in accordance with many embodiments.

FIG. 3B shows a mapped treatment region of the eye comprising the cornea, the posterior capsule, and the limbus. The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the center of the cornea to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 4A:
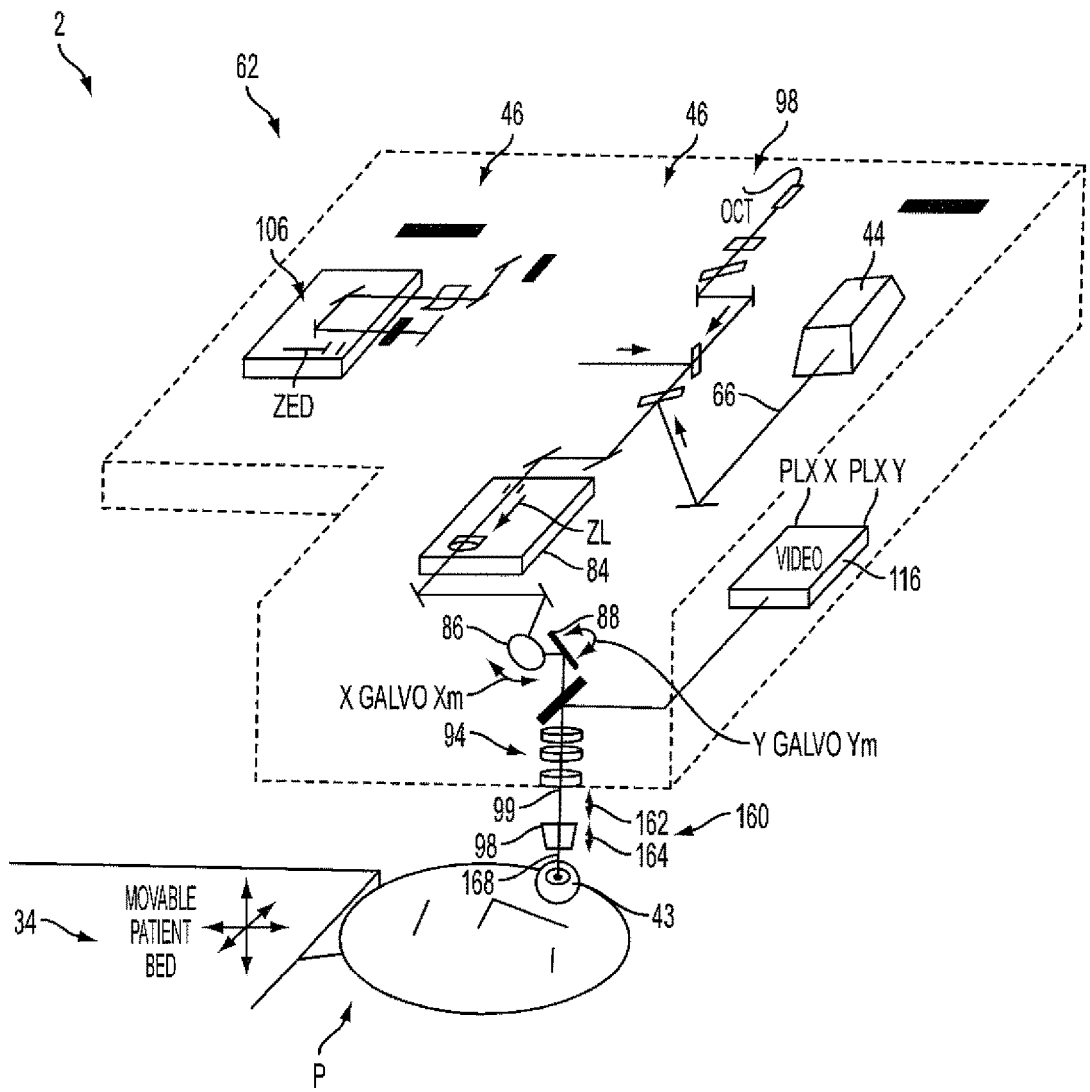
FIG. 4A shows correspondence among movable and sensor components of the laser delivery system, in accordance with many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
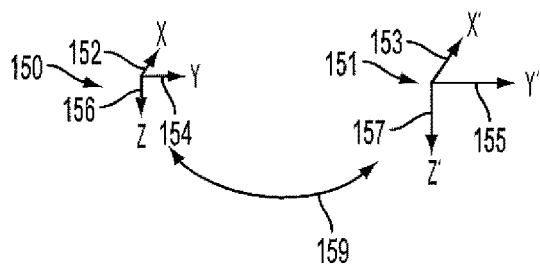
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments, the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. The group refractive index may be used and can take into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 mm. The group refractive index of 1.339 differs on the order of 1% for the OCT beam wavelength and spectral bandwidth. Many embodiments herein provide methods for determining the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 5A:
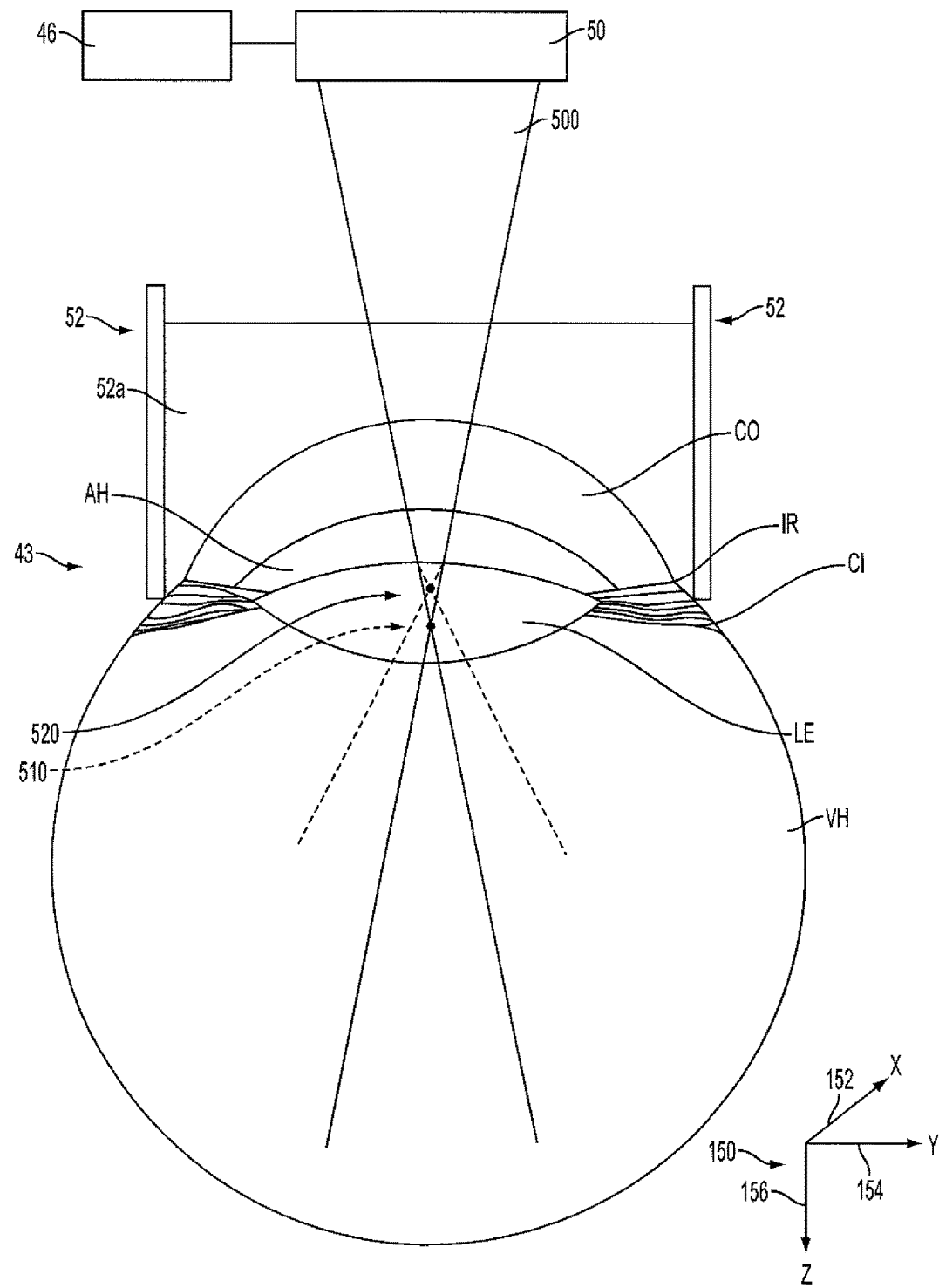
FIG. 5A shows a light source focused onto the lens of the eye to determine an index of refraction of the eye.

FIG. 5A shows light from shared optics 50 as directed by ranging subsystem 46 focused onto the lens LE of the eye 43. The beam 500 from shared optics 50 can be focused onto a target focal point 510 within the lens LE. The beam 500, however, may instead be focused onto a different target focal point within other anatomical locations in the eye 43 such as a tear film, a cornea CO, an aqueous humor AH, an anterior lens capsule, a lens cortex, an anterior portion of the lens cortex, a posterior portion of the lens cortex, a lens nucleus, a posterior lens capsule, or a vitreous humor VH. FIG. 5A also shows the iris IR and the ciliary muscles CI of the eye 43.

According to many embodiments, the ranging subsystem 46 of the system 2 can be used to determine the indices of refraction of the tissues of the eye 43. As shown in FIG. 5A, the eye 43 is coupled with the patient interface 52 which comprises a suitable liquid 52a (e.g., a sterile buffered saline solution (BSS) such as Alcon BSS (Alcon Part Number 351-55005-1) or equivalent) is disposed between and in contact with the patient interface lens posterior surface and the patient's cornea CO and forms part of a transmission path between the shared optics 50 and the patient's eye 43.

In many embodiments, the ranging subsystem 46 determines the location of the target focal point 510 in response to predetermined indices of refraction of the anatomical structures of the eye. One or more of the ranging subsystem 46 or the shared optics 50 may accounts for the indices of refraction of the structures between the shared optics 50 and the target focal point 510 to determine the configuration of the shared optics 50 to properly locate and focus the beam 500 onto the target focal point 510. For example, one or more of the XY-scan and Z-scan mechanisms of the shared optics 50 may be adjusted in response to the indices of refraction of the structures between the shared optics 60 and the target focal point 510. As shown in FIG. 5A, to focus the beam 500 onto the focal point 510 within the lens LE, the anatomical structures and materials that need to be taken into account include the suitable liquid 52a, the cornea CO, the aqueous humor AH, and the lens LE. The index of refraction of the suitable liquid 52a may be known or can be predetermined. The indices of refraction of the cornea CO and the aqueous humor AH typically do not vary significantly across individuals. The indices of refraction of the lens LE, however, can vary significantly across individuals. Further, the indices of refraction may vary even within the lens LE. The ranging subsystem 46 may first assume an index of refraction for the lens LE, for example, in response to an average lens index of refraction for a patient population. As shown in FIG. 5A, the target focal point 510 may actually be different than the actual focal point 520. Thus, the indices of refraction through the lens LE can be determined and the ranging subsystem 46 may further be configured to take into account the determined indices of refraction. As described herein, the positional differences between the target focal point 510 and the actual focal point 520 can be used to determine the index of refraction of at least a portion of the lens LE.

Figure 5B:
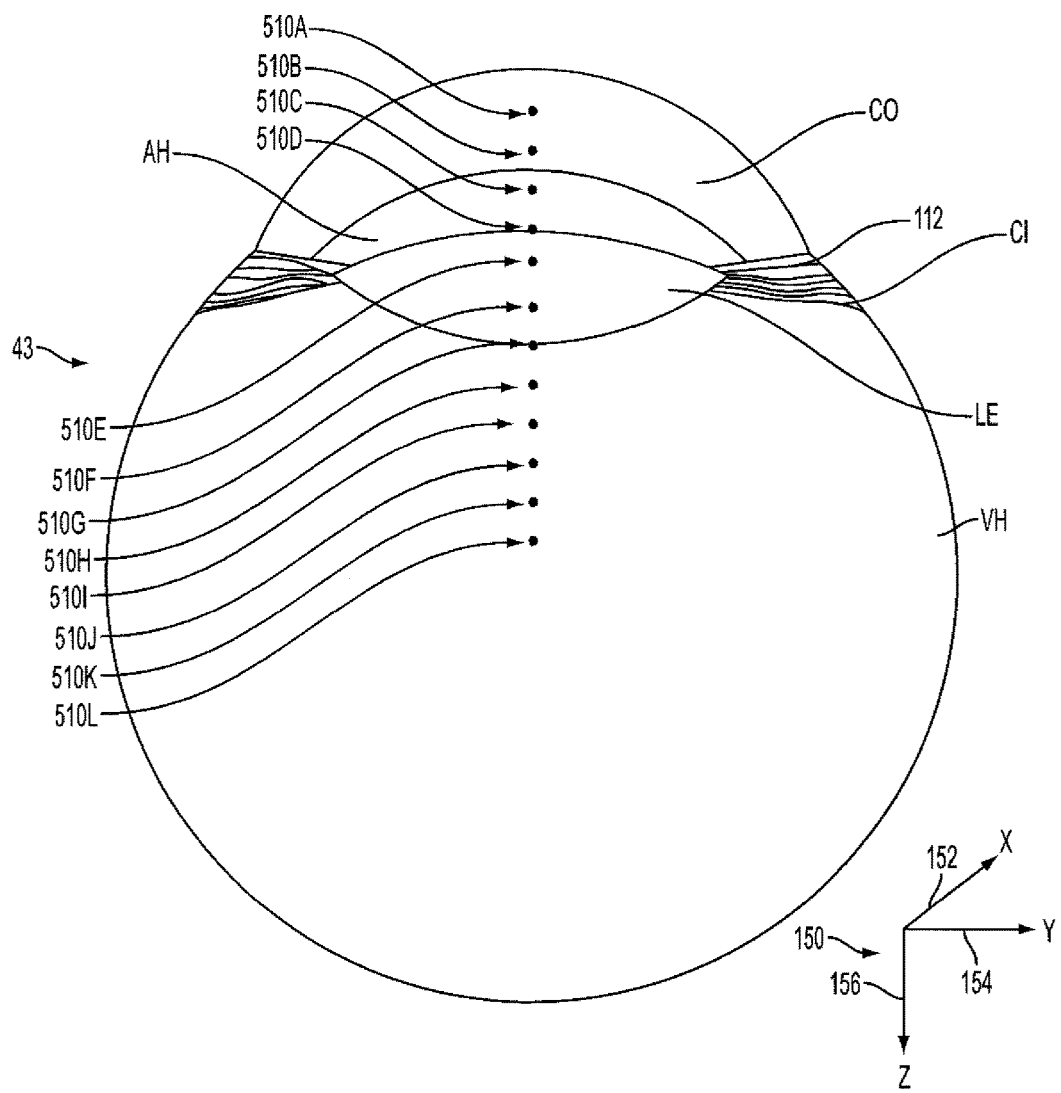
FIGS. 5B and 5C show focal points through various anatomical structures for determining indices of refraction of the various anatomical structures.

FIG. 5B show various target focal points 510A, 510B, 510C, 510D, 510E, 510F, 510G, 510H, 510I, 510J, 510K, and 510L through the anatomical structures of the eye EY for determining the indices of refraction of the various anatomical structures. As described here, one or more of the ranging subsystem 46 and the shared optics 50 may be used to determine the positional differences between each of these target focal points and their corresponding actual focal points to determine the index of refraction for the corresponding tissue structure of the eye. As shown in FIG. 5B, the target focal points 510A and 510B may be within the cornea CO; the target focal points 510C and 510D may be within or at the edge of the aqueous humor AH, the target focal points 510E, 510F, and 510G may be within or at the edge of the lens LE, and the target focal points 510H, 510I, 510J, 510K, and 510L may be within the vitreous humor VH.

Figure 5C:
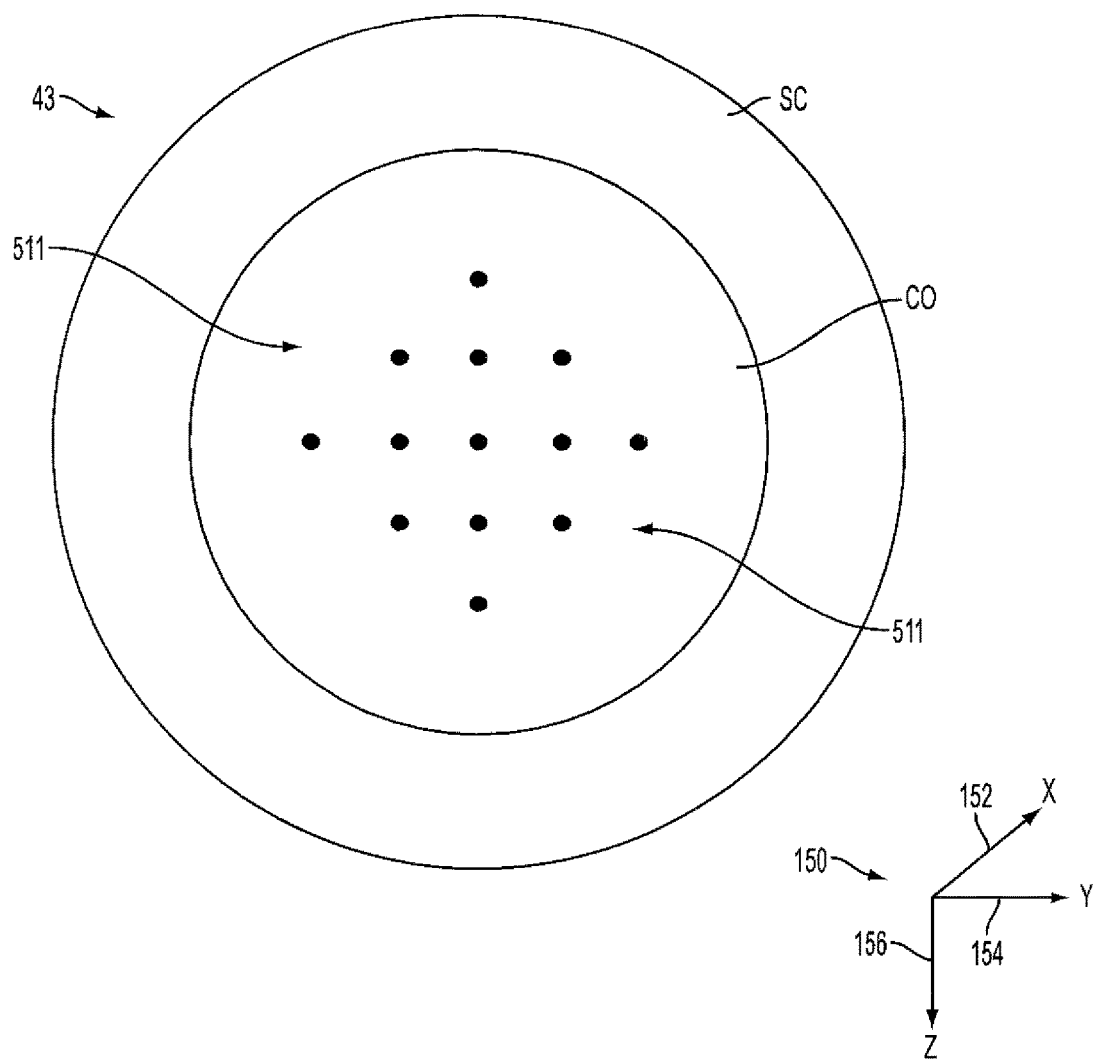

FIG. 5B shows the target focal points being varied along the vertical or Z-axis 156, for example by adjusting the shared optics 50. As shown in FIG. 5C, target focal points 511 may also be varied along the horizontal axes such as X-axis 152 and Y-axis 154. For example, by varying target focal points up to three dimensionally, i.e., across one or more of the X-axis 152, Y-axis 154, or Z-axis 156, up to a three-dimensional gradient index of refraction profile of an anatomical structure of the eye EY such as the lens LE may be generated. The laser eye surgery system 2 described herein may apply the refractive index profile of the lens LE to more accurately place target focal points within the anatomical structures of the eye which can lead to more precise laser incisions.

Figure 5D:
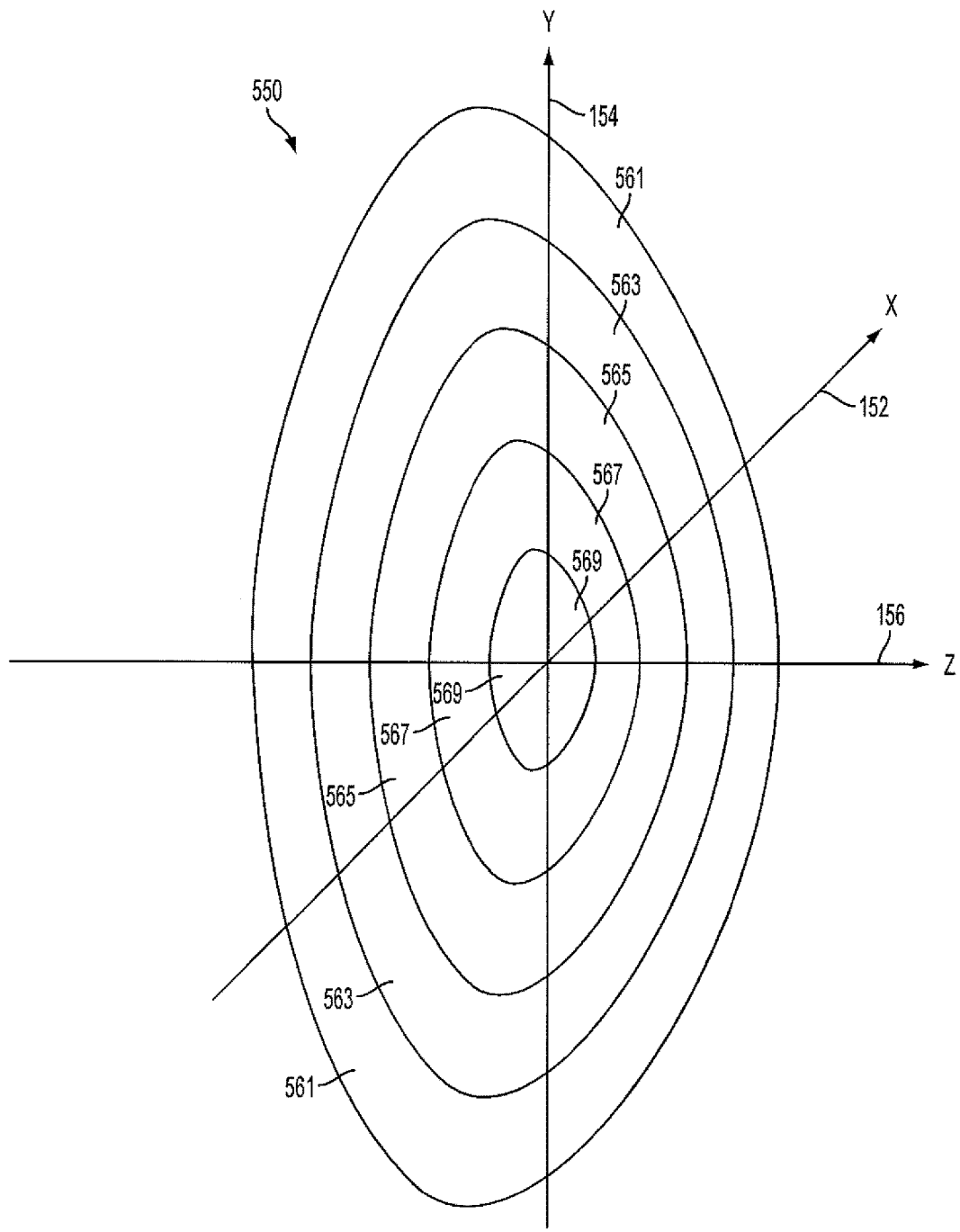
FIG. 5D shows a refractive index profile of a lens of an eye according to many embodiments.

FIG. 5D shows an exemplary refractive index profile 550 of the eye 43. FIG. 5D shows the profile 550 as two-dimensional, i.e., comprises refractive index information of the lens LE in response to position in the Y-axis 154 and the Z-axis 156. The profile 550 may in many embodiments be three-dimensional and comprise refractive index information of the lens LE further in response to position in the X-axis 152. In at least some cases, the indices of refraction in the lens LE may vary within the lens LE. As shown in FIG. 5D, the indices of refraction in the first lens region 561, the second lens region 563, the third lens region 565, the fourth lens region 567, and the fifth lens region 569 may be different from one another.

Figure 6:
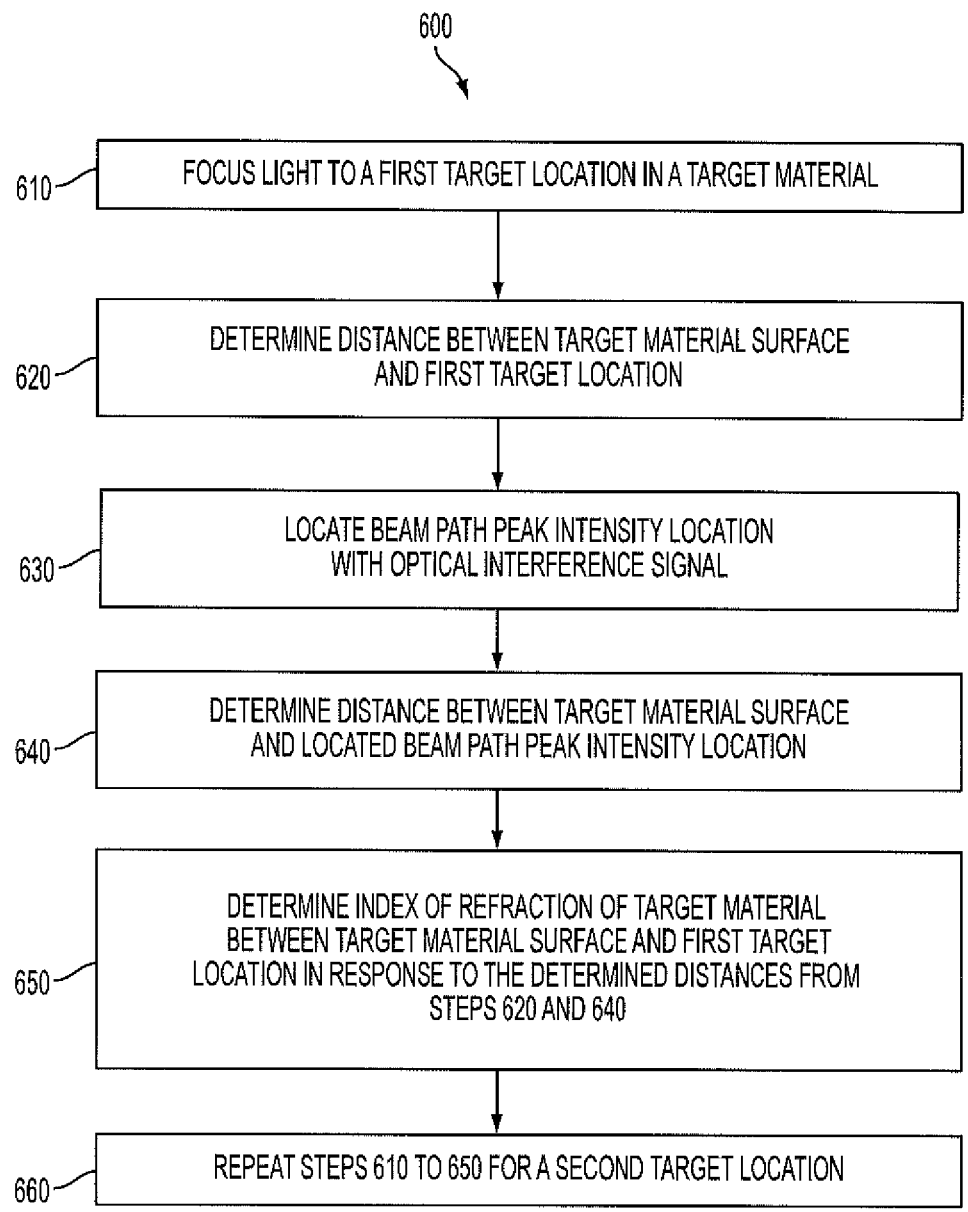
FIG. 6 shows a flow chart depicting a method for determining an index of refraction of a target material according to many embodiments.

FIG. 6 shows a flow chart depicting a method 600 for determining an index of refraction of a target material according to many embodiments.

In a step 610, light is focused to a first target location in a target material. As described herein, the focused light may comprise a beam 500, the first target location may comprise a target focal point 510, and the target material may comprise an anatomical structure of the eye 43 of a subject, such as the lens LE.

In a step 620, a distance between a surface of the target material and the first target location is determined. For example, the target material may comprise the lens LE and the surface of the target material may comprise the anterior surface of the lens LE. A user may direct the laser eye surgery system 2 to focus the beam 500 onto the target focal point 510. In response, the laser eye surgery system 2 may locate the target focal point 510 in response to predetermined refractive index data as described herein.

In many embodiments, the assumed index of refraction used by the laser eye surgery system 2 to calculate the position of the target focal point 510 may be referred to as $n_{assumed}$. The distance between the surface of the target material, e.g., the anterior surface of the lens LE, and the first target location, e.g., the target focal point 510, may be referred to as $D_{COMMAND}$. As described herein, the target focal point 510 may not be located in the same position as the actual focal point 520 due to refraction that the laser eye surgery system 2 and the ranging subsystem 46 may not account for. The distance between the surface of the target material, e.g., the anterior surface of the lens LE, and the actual focal point 520 may be referred to as $D_{ACTUAL}$. The actual index of refraction of the target material between the surface, e.g., the anterior surface of the lens LE, and the first target location, e.g., the target focal point 510, may be referred to as $n_{actual}$. In many embodiments, $D_{ACTUAL}$ is related to $D_{COMMAND}$ in accordance to the following equation: $D_{ACTUAL}=D_{COMMAND}*(n_{actual}/n_{assumed})$.

In a step 630, a peak intensity location of the beam path is located with an optical interference signal. For example, the ranging subsystem 46 may measure the intensity of the beam path along an axis, such as a vertical or Z-axis, through the target focal point 510 and may determine the location of peak intensity along this path. This peak intensity location may correspond to the location of the actual focal point 520.

In a step 640, a distance between the surface of the target material and the located beam path peak intensity location is determined. In many embodiments, an optical coherence tomography (OCT) system is used to determine intensity through the beam path. The distance between the surface of the target material, e.g., the anterior surface of the lens LE, and the located beam path peak intensity location may be referred to as $D_{OCT}$. As light may refract as it propagates through the target material to be read by the OCT system, the OCT system may account for this refraction using an assumed index of refraction which may be referred to as $n_{assumed}$. In many embodiments, $D_{OCT}$ is related to $DA_{CTUAL}$, in accordance with the following equation: $D_{OCT}=D_{ACTUAL}*(n_{actual}/n_{assumed})$.

In a step 650, the index of refraction of the target material between the target material surface and the first target location is determined in response to the determined distances from the steps 620 and 640. In many embodiments, this index of refraction comprises the average index of refraction of the material between the target material surface and the first target location. To determine this index of refraction, the above relationships or equations, $D_{ACTUAL}=D_{COMMAND}*(n_{actual}/n_{assumed})$ and $D_{OCT}=D_{ACTUAL}*(n_{actual}/n_{assumed})$, are applied. $D_{ACTUAL}$ is substituted for in the latter equation with the equivalent in the former equations to arrive at the equation: $D_{OCT}=D_{COMMAND}*(n_{actual}/n_{assumed})^2 \cdot n_{actual}$, or the index of refraction of the target material between the target material surface and the first target location, can then be calculated for using the rearranged equation: $n_{actual}=n_{assumed}*\sqrt{(D_{OCT}/D_{COMMAND})}$. The determined index of refraction can be mapped to the area of the lens of the eye.

In a step 660, the above steps 610 to 650 can be repeated for a second target location. The second target location may be in the same target material or a different target material. Also, instead of using the surface of the target material as the reference point for steps 620 and 640, the first target location may be used as the reference point for steps 620 and 640. As disclosed herein, the indices of refraction for a plurality of locations within a target material such as the lens LE can be measured to determine a refractive index profile of the target material, for example as shown in FIG. 5D.

One skilled in the art will appreciate that the above steps of the method 600 are by way of example. The ordering of the steps may be varied and one or more steps may be modified, added, or omitted without departing from the scope of the disclosure. A processor system of the laser eye surgery system 2 may comprise tangible medium embodying instructions for performing one or more steps of the method 600. Following the method 600, one or more of various surgical procedures may be performed on the eye. Such eye surgery procedures may include cataract surgery in response to the measured index or indices of refraction, retinal surgery in response to the measured index or indices of refraction, vitreo-retinal surgery in response to the measured index or indices of refraction, glaucoma surgery in response to the measured index or indices of refraction, refractive eye surgery in response to the measured index or indices of refraction, corneal surgery in response to the measured index or indices of refraction, and many other eye surgery procedures in response to the measured index or indices of refraction.

An example of refractive index measurement of an anatomical structure of the eye is now provided.

Figure 7:
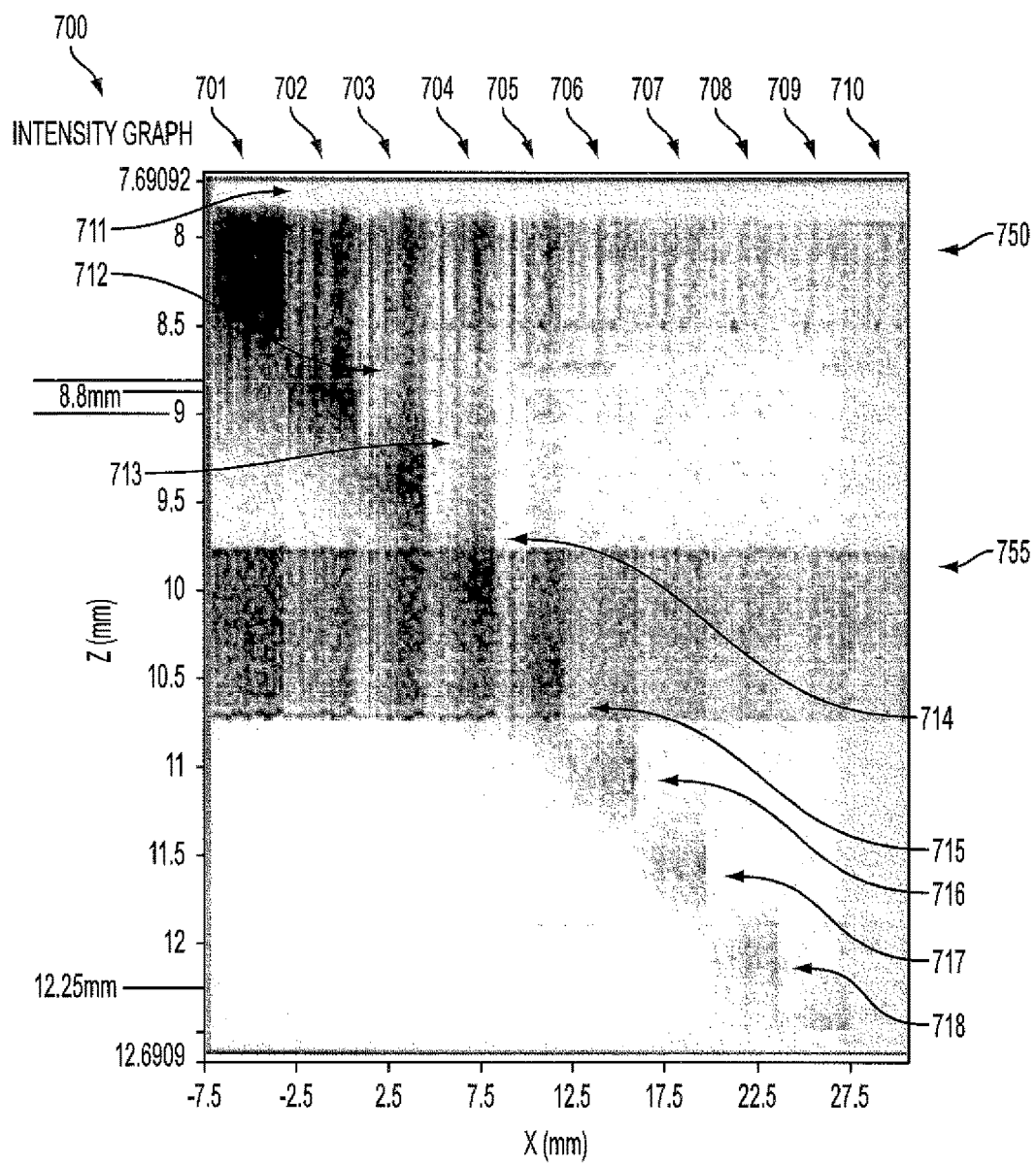
FIG. 7 shows an intensity graph of various beam paths through various anatomical structures of the eye for various desired focal points.

FIG. 7 shows an intensity graph 700 of various beam paths through various anatomical structures of the eye for various desired focal points. The beam path intensity profiles may be measured from the ranging subsystem 46 which may comprise an optical coherence tomography (OCT) system. The intensity graph 700 shows a first beam path intensity profile 701, a second beam path intensity profile 702, a third beam path intensity profile 703, a fourth beam path intensity profile 704, a fifth beam path intensity profile 705, a sixth beam path intensity profile 706, a seventh beam path intensity profile 707, an eight beam path intensity profile 708, a ninth beam path intensity profile 709, and a tenth beam path intensity profile 710. Each beam path intensity profile may correspond to a target focal point in the lens of an eye, with the higher numbered beam path profiles corresponding to deeper target focal points in the lens of the eye. For instance, the target focal point corresponding to the tenth beam profile 710 may be deeper than the target focal point corresponding to the ninth beam profile 709, which may be deeper than the target focal point corresponding to the eight beam profile 708, which may be deeper than the target focal point corresponding to the seventh beam profile 707, which may be deeper than the target focal point corresponding to the sixth beam profile 706, which may be deeper than the target focal point corresponding to the fifth beam profile 705, which may be deeper than the target focal point corresponding to the fourth beam profile 704, which may be deeper than the target focal point corresponding to the third beam profile 703, which may be deeper than the target focal point corresponding to the second beam profile 702, which may be deeper than the target focal point corresponding to the first beam profile 701. Each of these beam path intensity profiles may comprise a first high intensity band 750 and a second high intensity band 755. In many embodiments, the first and second high intensity bands 750, 755 comprise reflections from surfaces of one or more anatomical structures of the eye. For example, the first high intensity band 750 may comprise a reflection from the anterior surface of the cornea and the second high intensity band 755 may comprise a reflection from the posterior surface of the cornea.

The first beam path intensity profile 701 may comprise a peak intensity band 711 which may correspond to the focal point of the beam focused onto a first target focal point. The second beam path intensity profile 702 may comprise a peak intensity band 712 which may correspond to the focal point of the beam focused onto a second target focal point. The third beam path intensity profile 703 may comprise a peak intensity band 713 which may correspond to the focal point of the beam focused onto a third target focal point. The fourth beam path intensity profile 704 may comprise a peak intensity band 714 which may correspond to the focal point of the beam focused onto a fourth target focal point. The fifth beam path intensity profile 705 may comprise a peak intensity band 715 which may correspond to the focal point of the beam focused onto a fifth target focal point. The sixth beam path intensity profile 706 may comprise a peak intensity band 716 which may correspond to the focal point of the beam focused onto a sixth target focal point. The seventh beam path intensity profile 707 may comprise a peak intensity band 717 which may correspond to the focal point of the beam focused onto a seventh target focal point. The eight beam path intensity profile 708 may comprise a peak intensity band 718 which may correspond to the focal point of the beam focused onto an eighth target focal point. The ninth beam path intensity profile 709 may comprise a peak intensity band (not shown) which may correspond to the focal point of the beam focused onto a ninth target focal point. The tenth beam path intensity profile 710 may comprise a peak intensity band which may correspond to the focal point of the beam focused onto a tenth target focal point.

In the following example, the average index of refraction in the lens LE of the eye between two points can be calculated in response to the intensity graph 700. The peak intensity band 712 of the second beam path intensity profile 702 is located at a distance of 8.8 mm. The peak intensity band 718 of the eight beam profile 708 is located at a distance of 12.25 mm. The distance or difference between the two peak intensity bands 712 and 718 is therefore 3.45 mm. As described herein, this distance of 3.45 mm is regarded as $D_{OCT}$. The distance between the target focal point for the second beam path intensity profile 702 and the target focal point for the eight beam path intensity profile 708, or $D_{COMMAND}$, is 3 mm. That is, where the laser eye surgery system 2 is commanded to vary two focal points by 3 mm, the ranging subsystem 46 of the laser eye surgery system 2 detects the distance as 3.45 mm. As described herein, the index of refraction of the lens of the eye may be assumed. In this example, the assumed index of refraction, or $n_{assumed}$, is considered to be 1.3388. As described herein, the actual average index of refraction can be calculated in response to the aforementioned variables using the equation: $n_{actual} = n_{assumed} * \sqrt{D_{OCT}/D_{COMMAND}}$. In this example, $n_{actual}$, or the average index of refraction between the target focal points for the second beam path intensity profile 702 and the third beam path intensity profile 708, would therefore be 1.3388*sqrt(3.45/3) or 1.4357. As described herein, the indices of refraction of the lens LE of the eye and other structures of the eye may vary, and by generating a refractive index profile of the lens LE of the eye and other structures of the eye, a laser eye surgery system 2 can more accurately place laser beam focal points within the eye such as to more accurately place incisions.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method of determining an index of refraction of a material, the method comprising:
   focusing light from a light source along a beam path to a focal point having a location within the material, wherein the material comprises a surface adjacent a second material having a second index of refraction, the index of refraction of the material being different from the second index of refraction, and wherein the beam path extends a distance from the surface to the focal point; and
   determining the index of refraction of the material in response to the distance from the surface to the location of the focal point within the material.

2. The method of claim 1, wherein the material comprises a target material, the method further comprising:
   determining the location of the beam path with an optical interference signal of the focused light and wherein the location is determined in response to a location of a peak intensity of the optical interference signal.

3. The method of claim 2, wherein the target material comprises an optically transmissive tissue structure of an eye of a subject.

4. The method of claim 3, wherein the optically transmissive tissue structure of the eye comprises one or more of a tear film, a cornea, an aqueous humor, a lens, an anterior lens capsule, a lens cortex, an anterior portion of the lens cortex, a posterior portion of the lens cortex, a lens nucleus, a posterior lens capsule, or a vitreous humor and wherein a second tissue structure comprises the second material, the second tissue structure anterior to the optically transmissive tissue structure with the surface disposed in between.

5. The method of claim 3, further comprising determining a plurality of locations of a plurality of focal points along the beam path in order to determine the index of refraction of the optically transmissive tissue structure.

6. The method of claim 5, wherein the plurality of locations comprises a first location of a first focal point and a second location of a second focal point and wherein index of refraction corresponds to an average index of refraction of the material between the first point and the second point.

7. The method of claim 6, wherein the first location comprises an anterior location of an anterior portion of a lens of the eye and a second location comprises a posterior location of a posterior portion of the eye and wherein the index of refraction corresponds to an average index of refraction between the anterior portion of the lens and the posterior portion of the lens.

8. The method of claim 7, wherein the average index corresponds to an integral of the index of refraction along an optical path length between the anterior location and the posterior location in order to determine positioning of a treatment beam near a posterior capsule of the lens.

9. The method of claim 7, further comprising directing a plurality of focused laser beam pulses to a posterior portion of the lens to incise the posterior portion of the lens.

10. The method of claim 7, further comprising directing a plurality of focused laser beam pulses to a posterior capsule of the lens to incise the posterior capsule of the lens in response to the average index of refraction and wherein the focused beam comprises one or more wavelengths of light different than the focused laser beam.

11. The method of claim 5, further comprising mapping the index of refraction of the tissue structure in response to the plurality of locations of the plurality of focal points along the beam path, the method further comprising repeating the focusing and determining steps for each of the plurality of focal points in order to determine the index of refraction of the target material for said each of the plurality of locations.

12. The method of claim 11, wherein the plurality of locations comprise locations of the lens of the eye and wherein a gradient index profile of the lens of the eye is determined in response to the plurality of locations of the plurality of focal points within the lens of the eye.

13. The method of claim 2, wherein the light source comprises a light source of a tomography system, the tomography system comprising one or more of an optical coherence tomography system, a spectral optical coherence tomography system, a time domain optical coherence tomography system, a Scheimpflug imaging tomography system, a confocal tomography system, or a low coherence reflectometry system and wherein the location of the focal point is determined with the tomography system.

14. The method of claim 2, wherein the index of refraction of the target material is determined in response to a predetermined index of refraction.

15. The method of claim 14, wherein the predetermined index of refraction comprises the index of refraction of one or more of a patient interface optic, water, saline, cornea, or aqueous humor.

16. The method of claim 14, wherein calculating the index of refraction comprises multiplying the predetermined index of refraction with a square root of a distance between a surface of the target material and the determined beam path location divided by a distance between the surface of the target material and the intended focal point.

17. The method of claim 1,
wherein the step of focusing the light along the beam path to the focal point having a location within the material includes configuring an optical system according to a configuration, and using the optical system to direct the light to focus to the focal point, the focal point being an actual focal point of the light;

wherein the step of determining the index of refraction of the material comprises:

determining a target focal point location of the light corresponding to the configuration of the optical system and an assumed index of refraction of the material, and determining a first distance which is a distance between the target focal point location and the surface;

using a tomography system, measuring an optical interference signal of a light returned from the actual focal point, and based on the optical interference signal, determining a peak intensity location within the material which corresponds to a peak intensity of the optical interference signal;

determining a second distance which is a distance between the peak intensity location and the surface; and determining the index of refraction of the material based on the assumed index of refraction, the first distance, and the second distance.

18. The method of claim 17, wherein the index of refraction of the material is determined by calculating a product of the assumed index of refraction and a square root of a ratio of the second distance to the first distance.

19. The method of claim 18, and wherein the tomography system comprises one or more of an optical coherence tomography system, a spectral optical coherence tomography system, a time domain optical coherence tomography system, a Scheimpflug imaging tomography system, a confocal tomography system, or a low coherence reflectometry system.

20. The method of claim 17, wherein the material is an optically transmissive tissue structure of an eye of a subject.

* * * * *